United States Patent [19]

Oshima et al.

[11] 4,419,213

[45] Dec. 6, 1983

[54] OXYGEN SENSING ELEMENT FORMED AS LAMINATE OF THIN LAYERS ON SUBSTRATE PROVIDED WITH HEATER AND LEAD WIRES

[75] Inventors: Masaharu Oshima; Kenji Ikezawa; Hiroyuki Aoki, all of Yokosuka, Japan

[73] Assignee: Nissan Motor Company, Limited, Yokohama, Japan

[21] Appl. No.: 348,265

[22] Filed: Feb. 12, 1982

[30] Foreign Application Priority Data

Feb. 19, 1981 [JP] Japan ................................. 56-22242

[51] Int. Cl.[3] ............................................ G01N 27/58
[52] U.S. Cl. ...................................... 204/425; 204/426
[58] Field of Search .................... 204/195 S, 1 S, 425, 204/426; 123/489; 60/276; 422/94

[56] References Cited

U.S. PATENT DOCUMENTS

| | | | |
|---|---|---|---|
| 4,264,425 | 4/1981 | Kimura et al. | 204/195 S |
| 4,300,991 | 11/1981 | Chiba et al. | 204/195 S |
| 4,304,652 | 12/1981 | Chiba et al. | 204/195 S |

FOREIGN PATENT DOCUMENTS

| | | | |
|---|---|---|---|
| 2457489 | 12/1980 | France | 204/195 S |
| 2050628A | 5/1980 | United Kingdom | 204/195 S |
| 2052108 | 1/1981 | United Kingdom | 204/195 S |
| 2054163 | 2/1981 | United Kingdom | 204/195 S |

*Primary Examiner*—G. L. Kaplan
*Attorney, Agent, or Firm*—Schwartz, Jeffery, Schwaab, Mack, Blumenthal & Koch

[57] ABSTRACT

An oxygen sensing element of the type having a solid electrolyte oxygen concentration cell formed as a laminate of thin layers on a ceramic substrate in which a heater is embedded and end portions of lead wires are inserted. To enhance reliability of insulation between a lead wire through which heater current flows and lead wires connected to the concentration cell electrodes, the end portion of the heater lead wire is inserted into the substrate so as to make close contact with a terminal portion of the heater over substantially the entire length thereof and is completely shielded from environmental atmosphere by the substrate. Accordingly, even though a carbonaceous substance may be deposited on the substrate surface during practical use of the element, the possibility of heater current leaking of the concentration cell is obviated.

7 Claims, 14 Drawing Figures

OXYGEN SENSING ELEMENT FORMED AS LAMINATE OF THIN LAYERS ON SUBSTRATE PROVIDED WITH HEATER AND LEAD WIRES

BACKGROUND OF THE INVENTION

This invention relates to an oxygen sensing element of the type having a solid electrolyte oxygen concentration cell formed as a laminate of thin layers on a ceramic substrate, in which a heater is embedded and to which lead wires are attached.

In the automobile industry it has become familiar to install an oxygen sensor in the exhaust system as a means for detecting actual air/fuel ratio values in the engine. In most cases the oxygen sensor is of the oxygen concentration cell type utilizing an oxygen ion conductive solid electrolyte such as zirconia stabilized with calcia or yttria. In this field, a recent trend is to miniaturize the oxygen sensitive element of the sensor by constructing it as a laminate of thin, film-like layers on a ceramic substrate of very small size. The principal part of the laminate is a solid electrolyte layer and two electrode layers, namely, a reference electrode layer and a measurement electrode layer, formed adjacent the solid electrolyte layer. Usually an electric heater is embedded in the substrate to maintain the oxygen sensing element in operation at a sufficiently elevated temperature such as 600°–800° C. because the solid electrolyte concentration cell cannot properly function at temperatures below a certain level such as about 400° C.

An oxygen sensing element of this type has a plurality of lead wires connected respectively to the heater and the reference and measurement electrode layers. These lead wires are fixed to the ceramic substrate by embedding their end or tip portions in the substrate. To ensure electrical connection of each lead wire with a conductor of the heater or one of the electrode layers, usually a hole is formed in the substrate for each lead wire at a location where the end portion of the lead wire makes contact with the heater or electrode terminal, and the hole is filled with a conductive paste which is subsequently sintered to turn into a solid conductor.

Since an oxygen sensing element may be used to sense gas concentration in a combustion gas such as the exhaust gas of an automotive engine, it is inevitable that some carbon or certain carbonaceous substance will be deposited on the substrate surface where a surface of the aforementioned conductor in each hole is exposed. Sometimes the deposited carbon will provide a conductive path between a conductor and a lead wire through which a current flows to the heater and another conductor extending to a lead wire for one of the electrode layers. When current is supplied to the heater, the establishment of such a conductive path has an unfavorable influence on the accuracy of any measurement of electromotive force generated by the oxygen concentration cell. Moreover, particularly when a reference oxygen partial pressure at the interface between the reference electrode layer and the solid electrolyte layer is produced by externally supplying a DC current of a controlled intensity to the solid electrolyte layer as described in U.S. Pat. Nos. 4,207,159 and 4,224,113, any leakage of the heater current through the conductive path produced on the substrate surface is liable to cause a great increase in the current flowing through the solid electrolyte layer and, hence, a great increase in the magnitude of the reference oxygen partial pressure. As a result there arises a possibility of peeling of the reference electrode layer from the solid electrolyte layer or breaking of the solid electrolyte layer, whereby the oxygen sensing element tends to suffer from an unexpectedly short service life.

SUMMARY OF THE INVENTION

It is an object of the present invention to provide an improved oxygen sensing element of the type having a solid electrolyte oxygen concentration cell formed as a laminate of thin layers on a ceramic substrate in which a heater is embedded and to which lead wires are attached. It is a further object to provide an oxygen sensing element which has highly reliable electrical insulation between a lead wire through which a current flows to the heater and any of the lead wires connected to the electrode layers of the concentration cell so that the current for the heater never leaks to the oxygen concentration cell even if a conductive substance becomes deposited on the surface of the substrate during practical use of the element in combustion gases.

An oxygen sensing element according to the invention has a substrate made of a ceramic material, an oxygen concentration cell in the form of a laminate of thin layers including an oxygen ion conductive solid electrolyte layer, a reference electrode layer adjacent the solid electrolyte layer and a measurement electrode layer also adjacent the solid electrolyte layer, an electric heater embedded in the substrate and a plurality of lead wires of which tip portions are inserted into the substrate and respectively connected to the heater and the reference and measurement electrode layers. The element is characterized in that the inserted end portion of first one of the lead wires, through which current flows to the heater, is in close contact with a terminal portion of the heater substantially over the entire length of the inserted end portion and is completely shielded from environmental atmosphere by the substrate.

In practice, the substrate of the oxygen sensing element is produced by face-to-face bonding of two ceramic sheets one of which is first provided with the heater and the lead wires.

When, for example, the heater is a thin layer in the pattern of an elongate and meandering or zigzag path formed by printing of a conductive paste and subsequent sintering of the printed paste, the aforementioned terminal portion is made to have a relatively large width and to extend to one edge of the substrate, and the end portion of the lead wire through which current flows to the heater is embedded in the substrate so as to lie on this terminal portion of the heater.

The electrical connection between each of the remaining lead wires and either the other terminal portion of the heater or a terminal of one of the electrode layers may be established by utilizing a hole formed in the substrate and a conductor filled in the hole in the manner as described hereinbefore.

In the oxygen sensing element according to the invention, the electrical insulation between the lead wire through which a current flows to the heater and any of the lead wires connected to the oxygen concentration cell part of the element is not adversely affected even when conductive substances such as carbon becomes deposited on the surface of the substrate during practical use of the element. Therefore, the possibility of heater current leaking to the concentration cell is obviated. Accordingly, the electromotive force generated by the oxygen concentration cell can always be measured accurately. In the case of a reference oxygen partial pressure being produced in the oxygen concentration cell by the supply of a controlled current to the concentration cell, the possibility of an unfavorable increase in the magnitude of the reference oxygen partial pressure by heater current leaking to the concentration cell is obviated, and therefore the oxygen sensing element exhibits a very long service life.

DESCRIPTION OF THE PREFERRED EMBODIMENTS

First, a process of producing an oxygen sensing element embodying the present invention will be described with reference to FIGS. 1(A) to 1(G) because it is rather difficult to clearly understand the principal feature of the invention from the appearance of the completed oxygen sensing element.

Figure 1A:
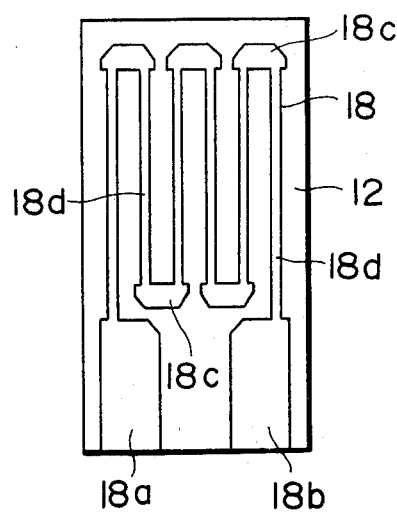
FIGS. 1(A) to 1(G) illustrate an exemplary process of producing an oxygen sensing element according to the invention.

Referring to FIG. 1(A), a rectangular sheet 12 (5 mm × 9 mm wide and 0.7 mm thick by way of example) of green or unfired alumina is used as a material for a plate-shaped ceramic substrate of the oxygen sensing element. For example, a green alumina sheet of a relatively large width can be formed by first preparing a wet composition containing an alumina powder optionally mixed with an auxiliary inorganic powder material such as talc, a binder such as polyvinyl butyral, a plasticizer such as dibutyl phthalate and a solvent such as ethanol or a mixture of ethanol and n-butanol, then shaping the wet composition into the form of a relatively wide sheet having a desired thickness by either an extrusion method or a so-called doctor-blade method, and drying the obtained sheet. The small rectangular sheet 12 is cut out of the dried but not yet fired alumina sheet.

The first step of producing an alumina substrate in which an electric heater is embedded is to apply a conductive paste onto a major surface of the green alumina sheet 12 by utilizing the technique of screen-printing so as to form a paste layer 18 in the pattern of an elongate and meandering or zigzag path. As a preferred example, the conductive paste contains 60 to 70% by weight of platinum powder dispersed in an organic liquid vehicle which is prepared by dissolving ethyl cellulose in terpineol with the addition of small amounts of dibutyl phthalate and a surface-active agent. It is preferred to form the illustrated paste layer 18 by the following two-stage printing method. At the first stage, the screen-printing of the conductive paste is so performed as to form only two terminal regions 18a and 18b and five turning regions 18c of the conducting path 18. The two terminal regions 18a, 18b are formed so as to terminate at one of the shorter side edges of the green alumina sheet 12. The printed paste is dried, for example, at about 80° C. for 30 min. In the dried state, the terminal regions 18a, 18b and the turning regions 18c have a common and uniform thickness of 16 μm for instance, and each of the two terminal regions 18a and 18b is about 1 mm in width and about 2.5 mm in length for instance. The second stage printing is so performed as to form narrow and straight linear regions 18d of the conducting path 18. For example, these linear regions 18d are all 12 μm in thickness and each 270 μm in width. The total length of the paste layer 18 and the width of the individual turning regions 18c are determined so that the heater given by sintering of the paste layer 18 may have an electric resistance of 5 to 6 ohms.

Figure 1B:
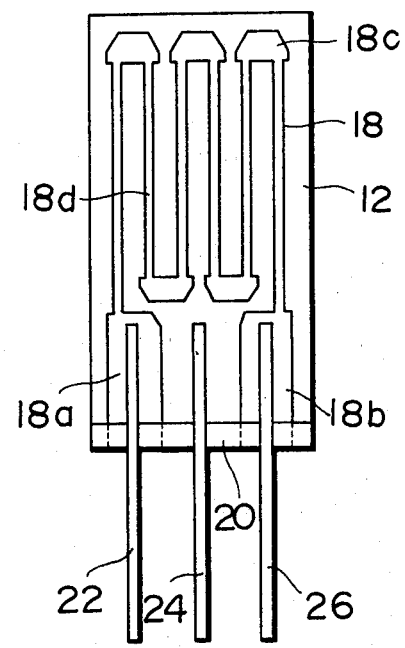

Referring to FIG. 1(B), a ceramic cement containing an alumina powder dispersed in an organic liquid vehicle is applied onto the surface of the green alumina sheet 12 so as to form an adhesive layer 20 along the short edge at which the two terminal regions 18a and 18b of the conductive paste layer 18 terminate. For example, the adhesive layer 20 is about 0.8 mm in width and about 0.3 mm in thickness.

Indicated at 22, 24 and 26 are three platinum wires (each 0.2 mm in diameter and about 7 mm in length for instance) employed as lead wires of the oxygen sensing element. In a parallel and spaced arrangement, tip portions (about 2 mm long) of these lead wires 22, 24, 26 are placed on the surface of the green alumina sheet 12 such that the end portions of the first and third lead wires 22 and 26 lie on the two terminal regions 18a and 18b of the conductive paste layer 18, respectively, while the tip portion of the second lead wire 24 lies in the middle between the two terminal regions 18a and 18b without making contact with any region of the conductive paste layer 18. Preferably, the end portions of these lead wires 22, 24, 26 are flattened in advance.

Figure 1C:
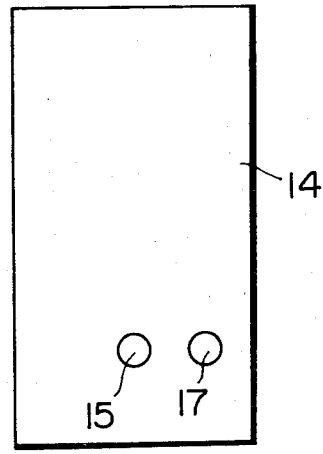

FIG. 1(C) shows another green alumina sheet 14 which is needed for completing the alumina substrate of the oxygen sensing element. This green alumina sheet 14 is similar in material and dimensions to the green alumina sheet 12 of FIG. 1(A), but two circular through-holes 15 and 17 are formed in an end region of this green alumina sheet 14. The center of each through-hole 15, 17 is at a distance of about 1.5 mm from the short side edge of the sheet 14, and the interval between these two holes 15 and 17 corresponds to the interval between the second and third lead wires 24 and 26 in FIG. 1(B).

Figure 1D:
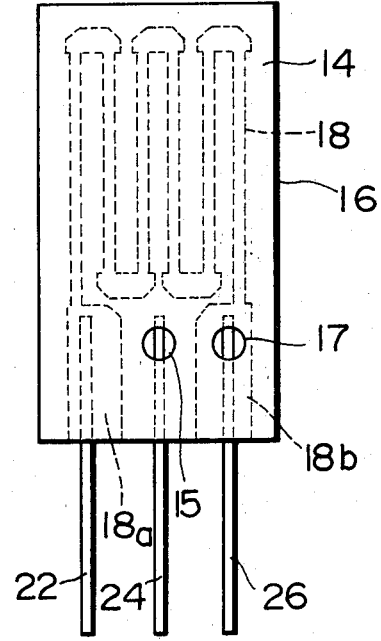

Referring to FIG. 1(D), the green alumina sheet 14 of FIG. 1(C) is placed on the other green alumina sheet 12 in the state of FIG. 1(B), and the two sheets 12 and 14 are bonded to each other by heating the piled two sheets 12 and 14 to about 100° C. and applying a pressure of about 3 kg/cm² for about 2 min. The steps illustrated by FIGS. 1(A) to 1(D) gives an unfired alumina substrate 16 which is provided with lead wires 22, 24, 26 and the dried platinum paste layer 18 to become a heater through a subsequent firing process. In the unfired substrate 16, the aforementioned two holes 15 and 17 are located just above the end portions of the second and third lead wires 24 and 26, respectively, so that the end portions of these two lead wires 24, 26 are partly exposed to the atmosphere through the respective holes 15 and 17. However, the end portion of the first lead wire 22 is completely covered with the overlaid green alumina sheet 14.

It is possible to produce an oxygen sensing element by first sintering the substrate 16 in the state of FIG. 1(D) and thereafter forming an oxygen concentration cell in the form of a laminate of thin layers on the surface of the sintered substrate, but in the illustrated process it is intended to first form an intermediate of the oxygen concentration cell in the form of a laminate of unfired layers on the surface of the unfired substrate 16 and to thereafter sinter the substrate and the intermediate of the concentration cell simultaneously.

Figure 1E:
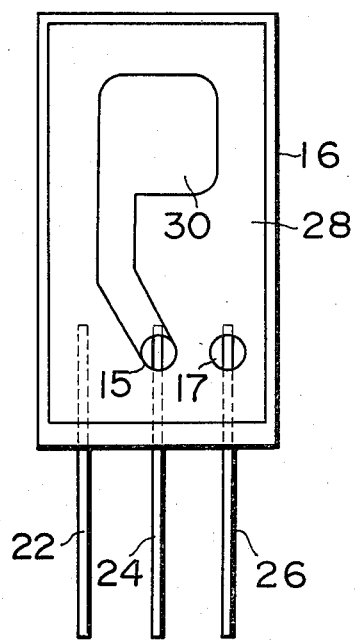

Referring to FIG. 1(E), a solid electrolyte paste prepared by dispersing 70 parts by weight of a powdered solid electrolyte material consisting of 95 mole% of zirconia and 5 mole% of yttria in 30 parts by weight of an organic liquid vehicle, which may be the same as the organic vehicle used in the aforementioned conductive paste, is applied onto the upper surface of the unfired substrate 16 by screen-printing so as to form a paste layer 28 over almost the entire surface area of the substrate 16. However, it is necessary to prevent the solid electrolyte paste from intruding into the holes 15 and 17 in the unfired substrate 16. The paste layer 28 is dried at about 100° C. for about 1 hr. It is suitable that the dried paste layer 28 has a thickness of about 10 $\mu$m.

Next, an electrically conductive cermet paste is applied onto the outer surface of the dried solid electrolyte layer 28 by screen-printing so as to form a cermet paste layer 30 in a pattern as shown in FIG. 1(E). An elongate arm region of this paste layer 30 extends to the periphery of the hole 15 located above the second lead wire 24 but does not intrude into this hole 15, though it is permissible that the inner wall of the hole 15 is partly covered with the cermet paste. For example, the conductive cermet paste is prepared by dispersing a mixture of 65 parts by weight of a platinum powder and 5 parts by weight of a zirconia-yttria powder (95:5 mole ratio) in 30 parts by weight of the organic liquid vehicle used in the aforementioned solid electrolyte paste. The conductive cermet paste 30 is dried at about 100° C. for about 1 hr. In the dried state, the thickness of this layer 30 is 13 $\mu$m for instance. Alternatively, a platinum paste may be used to form a conductive paste layer corresponding to the conductive cermet paste layer 30.

Figure 1F:
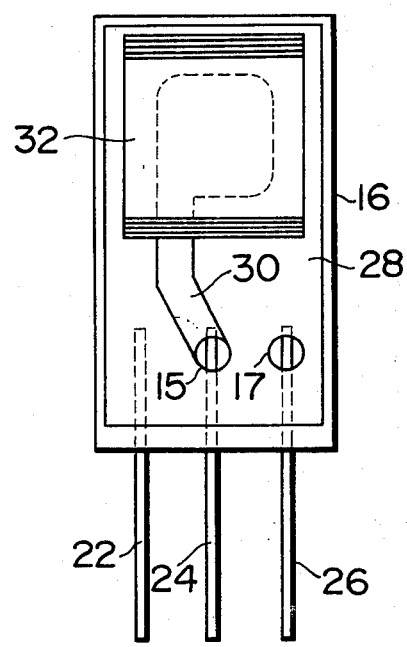

Referring to FIG. 1(F), the solid electrolyte paste mentioned with reference to FIG. 1(E) is applied onto the outer surfaces of the dried conductive cermet layer 30 and the dried solid electrolyte layer 28 by screen-printing so as to form an oxygen ion conductive solid electrolyte paste layer 32, which covers the entire surface area of the cermet layer 30 except the elongate arm region and makes close contact with the upper surface of the previously formed solid electrolyte layer 28 in a region surrounding the major periphery of the cermet layer 30. This solid electrolyte layer 32 is formed as a laminate of several thin layers by repeating screen-printing of the same paste so as to attain a total thickness of about 20 $\mu$m after drying at about 100° C. for about 1 hr. As can be seen in FIG. 1(F), it is preferred to perform the multi-stage screen-printing such that each of the laminated past layers is narrower in width than the directly underlying paste layer to result in that a stepped edge of the laminated solid electrolyte paste layer 32 intersects the arm region of the cermet layer 30. By forming this solid electrolyte paste layer 32 with the stepped edge, it can be avoided that the exudation of the liquid component of the solid electrolyte paste from this edge of the solid electrolyte paste layer 32 concentrates on a particular section of the cermet layer 30 and might damage the cermet layer 30.

Figure 1G:
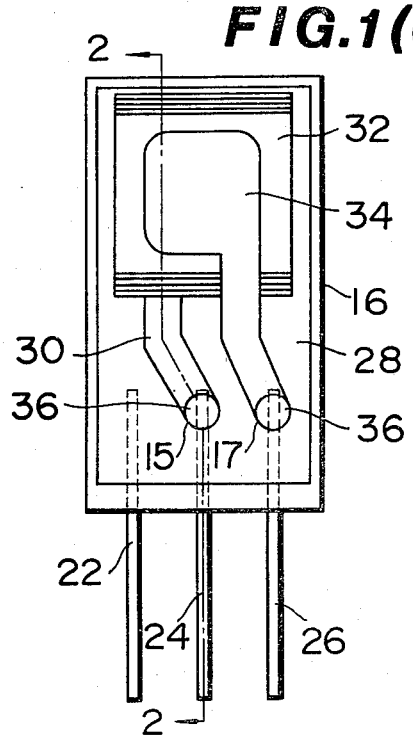

Referring to FIG. 1(G), the conductive cermet paste mentioned with reference to FIG. 1(E) is applied onto the outer surface of the dried solid electrolyte layer 32 by screen-printing so as to form a conductive cermet paste layer 34 in a pattern as shown in FIG. 1(G). This paste layer 34 has an elongate arm region which protrudes from the solid electrolyte layer 32 and comes into direct contact with the surface of the first formed solid electrolyte layer 28 to reach the periphery of the hole 17 located above the third lead wire 26. The screen-printing is so performed as to prevent the cermet paste from entering this hole 17, though it is permissible that the inner wall of the hole 17 be partly covered with the cermet paste. The conductive cermet paste layer 34 is dried at about 100° C. for about 1 hr. In the dried state, the thickness of this layer 34 is about 10 $\mu$m for instance.

To establish electrical connection between the second lead wire 24 and the conductive cermet layer 30 and also between the third lead wire 26 and the conductive cermet layer 34, the two holes 15 and 17 are completely filled with a conductive paste indicated at 36 in FIG. 1(G). For example, the conductive paste is prepared by dispersing 70 parts by weight of a powder mixture of 71 Wt% of platinum and 29 Wt% of $\alpha$-alumina in 30 parts by weight of the organic liquid vehicle used in the peviously described pastes. The conductive paste 36 in the holes 15 and 17 are dried at about 100° C. for about 1 hr.

The unfired element in the state of FIG. 1(G) is fired in air at about 1500° C. for about 2 hr to simultaneously sinter the substrate 16, platinum layer 18 in the substrate 16, the laminate of the dried paste layers 28, 30, 32, 34 formed on the substrate 16, and the dried conductive paste 36 in the holes 15 and 17.

Figure 2:
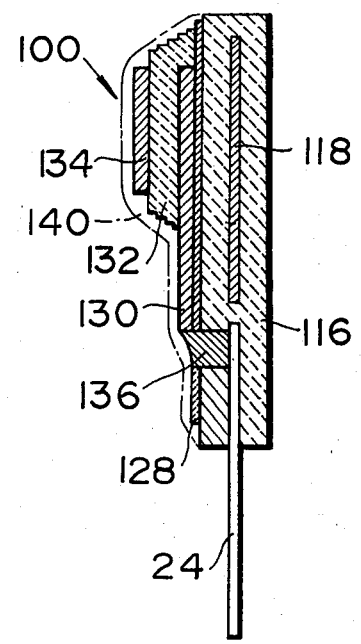
FIG. 2 is a schematic and sectional view of an oxygen sensing element produced by the process illustrated in FIGS. 1(A) to 1(G)

FIG. 2 is a view corresponding to the section taken along the line 2—2 in FIG. 1(G) and shows an oxygen sensing element 100 obtained upon completion of the aforementioned simultaneous sintering operation. The unfired substrate 16 in FIG. 1(G) turns into a rigid alumina substrate 116 of the oxygen sensing element 100 and the platinum layer 18 in the unfired substrate 16 into a heater layer 118. Simultaneously, the solid electrolyte layer 28, conductive cermet layer 30, solid electrolyte layer 32 and conductive cermet layer 34 in FIG. 1(G) turn into sintered solid electrolyte layer 128, sintered cermet electrode layer 130, sintered solid electrolyte layer 132 and sintered cermet electrode layer 134, respectively, while the conductive paste 36 in the holes 15 and 17 turns into sintered conductors 136.

As is known, the inner electrode layer 130 which is often called reference electrode layer, the oxygen ion conductive solid electrolyte layer 132 and the outer electrode layer 134, which is often called measurement electrode layer, constitute an oxygen concentration cell that generates an electromotive force whenever there is a difference between an oxygen partial pressure at the outer electrode side of the solid electrolyte layer 132 and an oxygen partial pressure at the inner electrode side of the solid electrolyte layer 132. These three layers 130, 132, 134 are all microscopically porous and permeable to gases. The solid electrolyte layer 128 is not essential to the oxygen concentration cell, but this layer 128 is added with a view to enhancing the strength of adhesion of the laminated concentration cell to the ceramic substrate 116.

Usually the outer surfaces of the sintered laminate on the substrate 116 are covered with a porous protecting layer 140 formed of a ceramic material. For example, the porous protecting layer 140 is formed by plasma-spraying a spinel powder to a thickness of 50 to 70 $\mu$m. Preferably, a thin film (not shown, about 0.5 $\mu$m) of platinum or an alternative electrode material may be deposited on the outer surface of the measurement electrode layer 134 by a physical vapor deposition method such as sputtering or vacuum evaporation prior to the formation of the protecting layer 140. The addition of such a metal film has the effect of improving the sensitivity or responsiveness of the oxygen sensing element because of a substantial increase in the effective surface area of the measurement electrode layer and, hence, an increase in the so-called triple-phase points where a gas subject to measurement, the measurement electrode layer and the oxygen ion conductive solid electrolyte layer come into contact with one another.

Figure 3:
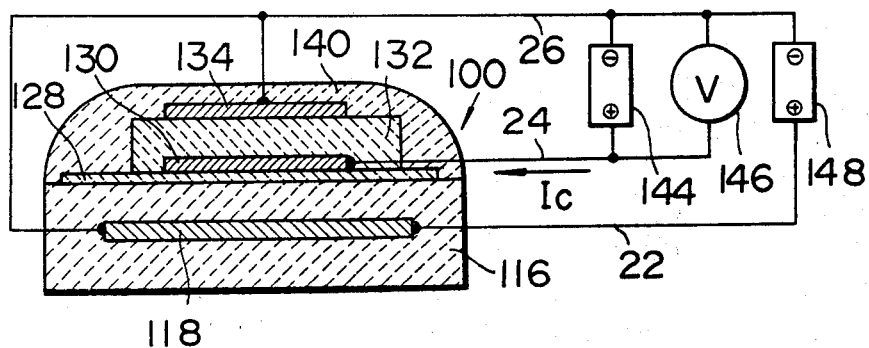
FIG. 3 is an explanatory illustration of an oxygen sensing device including the oxygen sensing element of FIG. 2.

FIG. 3 shows the principle of an oxygen sensing device which utilizes the oxygen sensing element 100 of FIG. 2 as a probe. In this device, the inner or reference electrode layer 130 of the oxygen sensing element 100 is connected to the positive terminal of a DC power supply 144 via the second lead wire 24 and the outer or measurement electrode layer 134 to the negative terminal of the power supply 144 via the third lead wire 26, and a voltage measuring device 146 is connected to the reference and measurement electrode layers 130 and 134 by using the second and third lead wires 24 and 26. There is another DC power supply 148, and the positive terminal of this power supply 148 is connected to one terminal of the heater layer 118 in the oxygen sensing element 100 via the first lead wire 22 and the negative terminal to the other terminal of the heater layer 118 via the third lead wire 26. Thus, the third lead wire 26 is used as a grounding lead common to the heater 118 and the oxygen concentration cell in the oxygen sensing element 100.

As described in U.S. Pat. No. 4,224,113, a reference oxygen partial pressure of an adequate magnitude can be produced and maintained at the interface between the reference electrode layer 130 and the oxygen ion conductive solid electrolyte layer 132, while the measurement electrode layer 134 is exposed through the porous protective layer 140 to an oxygen-containing gas atmosphere, by using the DC power supply 144 to force a DC current $I_c$ of a controlled intensity to flow through the solid electrolyte layer 132 from the reference electrode layer 130 toward the measurement electrode layer 134. The flow of the current $I_c$ in the solid electrolyte layer 132 causes migration of oxygen ions through this solid electrolyte layer 132 from the measurement electrode layer 134 toward the reference electrode layer 130. As a joint effect of the migration of oxygen ions and diffusion of oxygen molecules formed at the reference electrode layer 130 toward the reference electrode layer 134 through the microscopically porous solid electrolyte layer 132, a practically constant oxygen partial pressure can be maintained at the interface between the reference electrode layer 130 and the solid electrolyte layer 132. Therefore, the oxygen concentration cell in the element 100 generates an electromotive force the magnitude of which depends on the difference between the reference oxygen partial pressure in the element 100 and an oxygen partial pressure in the gas atmosphere to which the measurement electrode layer 134 is exposed.

The voltage measuring device 146 is used to measure an output voltage of the oxygen sensing element 100 between the reference and measurement electrode layers 130 and 134 to thereby detect the concentration of oxygen in the gas atmosphere in which the oxygen sensing element 100 is disposed. Since a solid electrolyte oxygen concentration cell of this catagory operates properly only at sufficiently elevated temperatures, the power supply 148 keeps the heater layer 118 in the oxygen sensing element 100 energized (except when the element 100 is disposed in a sufficiently hot gas atmosphere) so as to maintain the element 100 usually at about 600° C.

The primary feature of the oxygen sensing element 100 according to the invention resides in the manner of electrical and mechanical connection of the first lead wire 22 with the heater layer 118. As can be seen in FIGS. 1(B) and 1(D), the tip portion of the first lead wire 22 is embedded in the unfired substrate 16 by placing the end portion of the wire 22 on the sufficiently widened terminal region 18a of the conductive paste layer 18 which becomes the heater layer 118, so that the connection between this lead wire 22 and the heater layer 118 becomes very sure and stable. More importantly the embedded end portion of the lead wire 22 is completely shielded from the environmental atmosphere by the assembly 16 of the two green alumina sheets 12, 14 without using any conductive material in achieving the shielding. As a result of such shielding, even if conductive substances such as carbon, deposited on the surface of the substrate 116 or on the solid electrolyte layer 128 through the porous protective layer 140 of the oxygen sensing element 100 in practical operation and came into contact with the conductor 136 in the hole 15 above the second lead wire 24, the heating current flowing from the first lead wire 22 to the heater layer 118 will not leak to the second lead wire 24 or to the reference electrode layer 130. Therefore, the control current $I_c$ supplied to the oxygen concentration cell is not influenced by the current supplied to the heater element 118 even though the oxygen sensing element 100 is used in a combustion gas containing some free carbon or certain carbonaceous substances that are electrically conductive.

As mentioned hereinbefore, if the heating current leaks out to the solid electrolyte layer 132 through the reference electrode layer 130 it becomes probable that either the reference electrode layer 130 or the solid electrolyte layer 132 will be damaged by the effect of a great rise in the oxygen partial pressure at the interface between the reference electrode layer 130 and the solid electrolyte layer 132. The oxygen sensing element 100 of the present invention does not suffer from such a phenomenon and, hence, exhibits a very long service life. In addition, the measurement of the output voltage of the oxygen sensing element 100 is not rendered inaccurate by heater current leaks.

The above described feature of the invention will more clearly be recognized when contrasted with a conventional method of connecting the first lead wire to the heater layer in producing an oxygen sensing element fundamentally analogous to the element 100 of FIG. 2, the conventional method being illustrated in FIGS. 5(A) to 5(D).

Figure 5A:
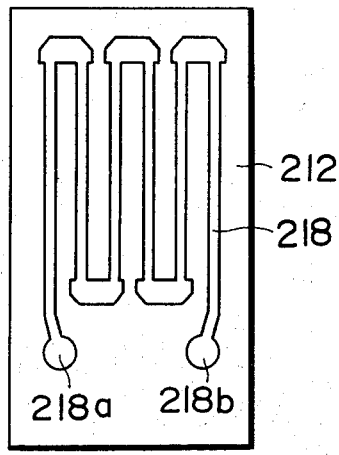
FIGS. 5(A) to 5(D) illustrate a process of producing a known oxygen sensing element for comparison with the process illustrated in FIGS. 1(A) to 1(G).
Figure 5B:
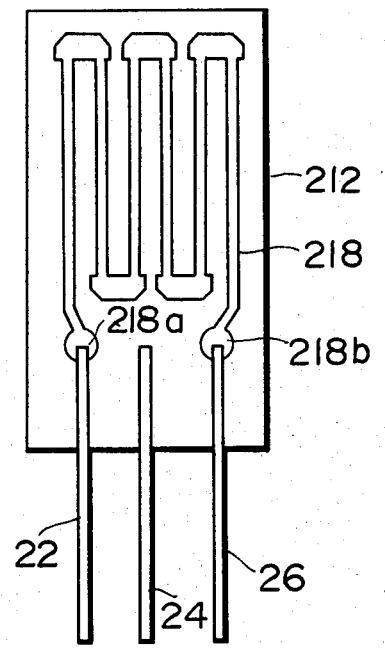

Referring to FIG. 5(A), a platinum paste is applied onto a major surface of a green alumina sheet 212 so as to form a paste layer 218 in the pattern of an elongate and meandering or zigzag path. This conductive paste layer 218 terminates at some distance from one of the shorter side edges of the sheet 212 so as to form two terminal regions 218a and 218b which are not so wide as the terminal regions 18a and 18b in FIG. 1(A). In this case, end portions of the three lead wires 22, 24, 26 are placed on the green alumina sheet 212 in the manner as shown in FIG. 5(B). That is, the ends of the first and third lead wires 22 and 26 are positioned respectively on the two terminal regions 218a and 218b of the conductive paste layer 218.

Figure 5C:
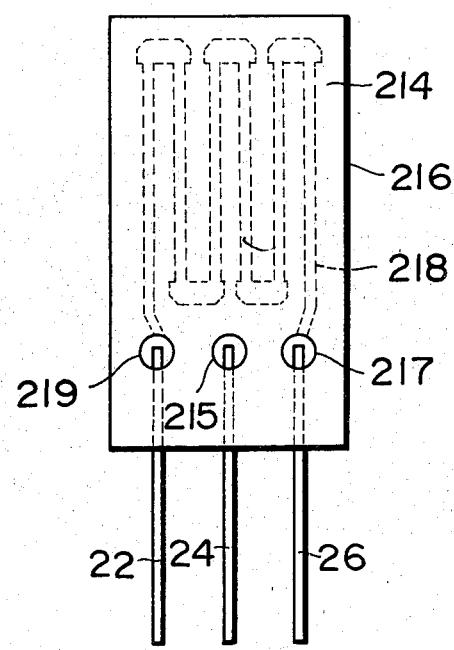

Referring to FIG. 5(C), another green alumina sheet 214 needful for completing the substrate of the oxygen sensing element is formed with three throughholes 215, 217 and 219. The holes 215 and 217 are the counterparts of the holes 15 and 17 in FIGS. 1(C) and 1(D). The additional hole 219 is located such that, when the green alumina sheet 214 is placed on the other green alumina sheet 212, the terminal region 218a of the conductive paste layer 218 and the end of the first lead wire 22 can be seen through this hole 219.

Figure 5D:
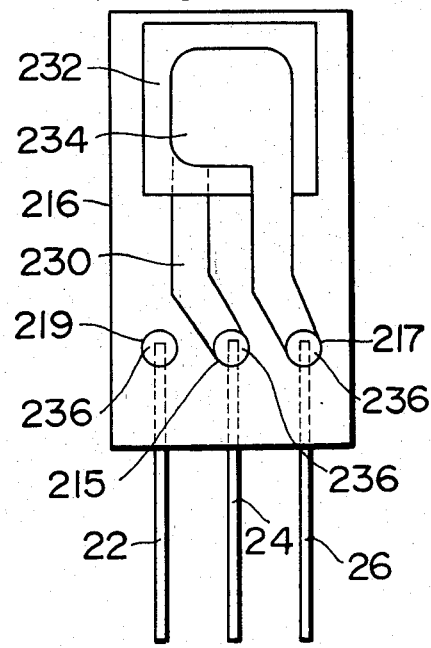

Referring to FIG. 5(D), a conductive cermet layer 230 is formed on the outer surface of the unfired substrate 216 shown in FIG. 5(C) so as to have an elongate arm region extending to the periphery of the hole 215 located above the second lead wire 24. (In this case, the counterpart of the solid electrolyte layer 28 in FIG. 1(G) is omitted for simplicity.) After drying of this paste layer 230, an oxygen ion conductive solid electrolyte paste layer 232 is formed so as to entirely cover the conductive cermet layer 230 except its arm region, and another conductive cermet paste layer 234 is formed on the outer surface of the dried solid electrolyte layer 232 so as to have an arm region extending to the periphery of the hole 217 located above the third lead wire 26. After that, all the holes 215, 217, 219 in the unfired substrate 216 are filled with a conductive paste indicated at 236.

The element in the state of FIG. 5(D) is fired so as to achieve simultaneous sintering of the substrate 216, platinum layer 218 in the substrate 216, the laminate of three layers 230, 232, 234 on the substrate 216 and the conductor 236 in the three holes 215, 217, 219.

In the case of the oxygen sensing element produced by the process illustrated in FIGS. 5(A) to 5(D), the deposition of carbon or any other conductive substance on the surface of the substrate is liable to provide a conductive path between the conductor (236) in the hole 219 located above the first lead wire 22 and the conductor (236) in the hole 215 located above the second lead wire 24. Then the current being supplied to the heater layer (218) will leak to the reference electrode layer (230) to the effect of greatly increasing the current flowing through the solid electrolyte layer (232) and, therefore, greatly increasing the magnitude of the oxygen partial pressure at the interface between the reference electrode layer and the solid electrolyte layer. Therefore, this oxygen sensing element has a short service life and tends to suffer a high failure rate.

Figure 4:
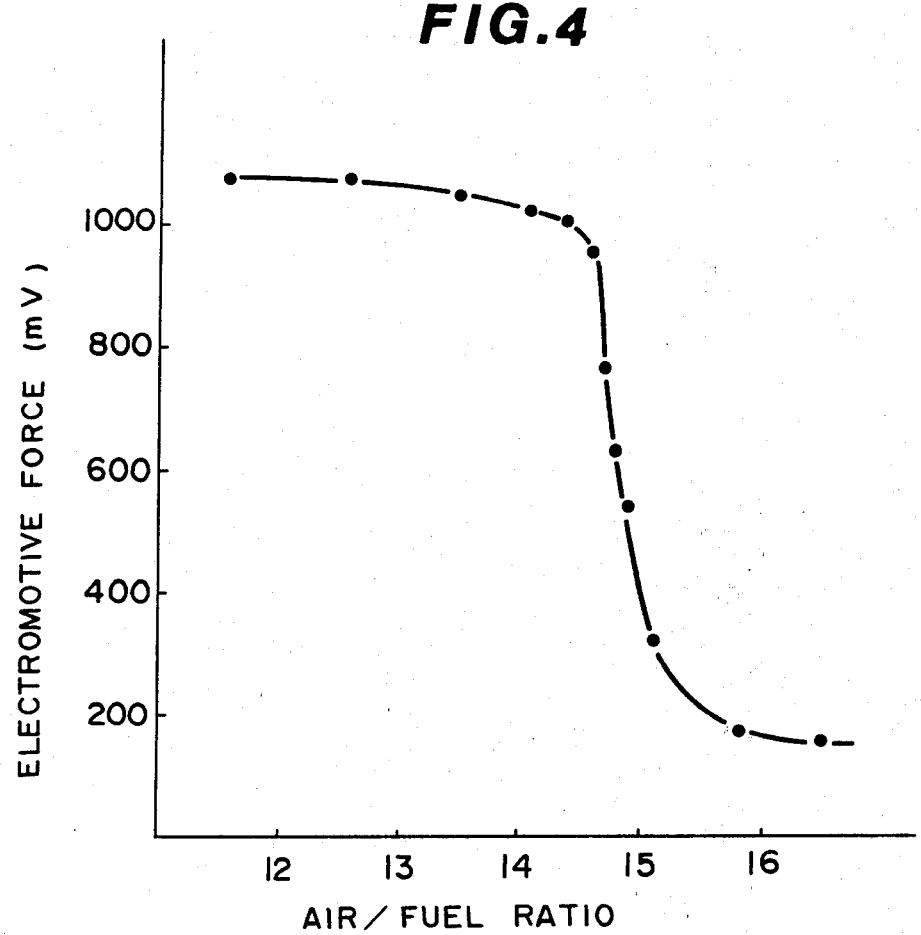
FIG. 4 is a graph showing the output characteristic of the oxygen sensing element in the device of FIG. 3 observed when the device was used in exhaust gases of an automotive internal combustion engine which was operated at various air/fuel ratio values.

An experiment was carried out to examine durability of the oxygen sensing element 100 according to the invention produced by the method illustrated in FIGS. 1(A) to 1(G). The oxygen sensing element was disposed in the exhaust pipe of a 2-liter gasoline engine installed on an automobile as the probe of the device shown in FIG. 3, and the engine was operated with a fuel-rich air-fuel mixture for a total period of time in which the automobile could have travelled a total distance of 10000 km. A number of samples of the oxygen sensing element 100 were tested under the same condition. For comparison, the same number of samples of the similarly designed oxygen sensing element were produced by the method illustrated in FIGS. 5(A) to 5(D) and tested similarly. Initially, the relationship between the air/fuel ratio (by weight) of the mixture fed to the engine and the magnitude of the electromotive force generated by every oxygen sensing element sample in the exhaust pipe was as shown in FIG. 4 irrespective of the method of producing the sample. After the test, the oxygen sensing element samples according to the invention exhibited practically no change in their output characteristic, but about 35% of the samples produced by the method of FIGS. 5(A) to 5(D) were judged to have significantly deteriorated because the magnitude of the electromotive force generated by these samples at air/fuel ratio values of 12–14 remained below 1000 mV.

Needless to mention, the construction of the illustrated oxygen sensing element 100 should be taken as by way of example. The present invention places no restriction on the particulars of the oxygen concentration cell formed on the substrate. As a different example, both the reference electrode layer and the measurement electrode layer of the concentration cell may be formed on the outer surface of the oxygen ion conductive solid electrolyte layer (corresponding to 132 in FIG. 2) so as to be spaced from each other, with the provision of a gasimpermeable shield layer only on the reference electrode layer. As a still different example, the concentration cell may include an oxygen source layer such as a Ni-NiO mixture layer adjacent the reference electrode layer for the purpose of producing a reference oxygen partial pressure without externally supplying a current to the concentration cell. Also it is optional to modify the heater layer 118 in the illustrated embodiment by using a thin metal wire or a strip of a metal foil as the material of the heater embedded in the substrate.

The embodiment was chosen and described in order to best explain the principles of the invention and its practical application to thereby enable others to utilize the invention in various embodiments with various modifications as are suited to the particular use contemplated. It is intended that the scope of the invention be defined by the appended claims.

What is claimed is:

1. An oxygen sensing element having a substrate comprising a ceramic material, an oxygen concentration cell in the form of a laminate of thin layers placed on a major surface of the substrate, said laminate including an oxygen ion conductive solid electrolyte layer, a reference electrode layer adjacent the solid electrolyte layer and a measurement electrode layer adjacent the solid electrolyte layer, an electric heater embedded in the substrate and a plurality of lead wires having end portions inserted into the substrate and respectively connected to the heater and the reference and measurement electrode layers, wherein the electrical connection of each of the lead wires connected to said concentration cell includes a conductor filled hole formed in the substrate so as to open at said surface of the substrate, and wherein the inserted end portion of a first one of the lead wires, through which a current flows to the heater, is in close contact with a terminal portion of the heater substantially over the entire length of the inserted end portion and is completely shielded from environmental atmosphere by the substrate.

2. An oxygen sensing element according to claim 1, wherein said terminal portion of the heater reaches an edge of the substrate, said end portion of said first one of the lead wires being inserted into the substrate from said edge so as to lie on said terminal portion of the heater.

3. An oxygen sensing element according to claim 2, wherein the substrate is formed by face-to-face bonding of two sheets, one of which is first provided with said heater on a major surface thereof, the end portions of the lead wires being tightly sandwiched between the bonded two sheets.

4. An oxygen sensing element according to claim 3, wherein the heater is a thin layer formed by sintering a layer of a paste containing a powdered conductive material on said surface of said one of said two sheets.

5. An oxygen sensing element according to claim 4, wherein the heater has a form comprising an elongate path, said terminal portion of the heater being larger in width than the remaining portion of the heater.

6. An oxygen sensing element according to claim 2 or 5, wherein said end portion of said one of the lead wires is flattened.

7. An oxygen sensing element according to claim 1, wherein second one of said plurality of lead wires is connected to the other terminal portion of the heater by a conductor filled in a hole formed in the substrate so as to open at said surface of the substrate.

* * * * *